United States Patent
Chang et al.

(10) Patent No.: US 11,602,299 B2
(45) Date of Patent: Mar. 14, 2023

(54) METHOD AND SYSTEM FOR PROCESSING ELECTROENCEPHALOGRAM SIGNAL

(71) Applicant: A-Neuron Electronic Corporation, Hsinchu County (TW)

(72) Inventors: Chia-Chi Chang, Taipei (TW); Pei-Chen Lin, Hsinchu (TW); Yue-Loong Hsin, Taichung (TW)

(73) Assignee: A-Neuron Electronic Corporation, Hsinchu County (TW)

( * ) Notice: Subject to any disclaimer, the term of this patent is extended or adjusted under 35 U.S.C. 154(b) by 269 days.

(21) Appl. No.: 16/903,343

(22) Filed: Jun. 16, 2020

(65) Prior Publication Data

US 2021/0386311 A1   Dec. 16, 2021

(51) Int. Cl.
| | |
|---|---|
| A61B 5/00 | (2006.01) |
| A61B 5/374 | (2021.01) |
| G16H 50/30 | (2018.01) |
| A61B 5/316 | (2021.01) |

(52) U.S. Cl.
CPC .............. *A61B 5/374* (2021.01); *A61B 5/316* (2021.01); *G16H 50/30* (2018.01)

(58) Field of Classification Search
CPC ................................ A61B 5/374; A61B 5/316
USPC ......................................................... 600/544
See application file for complete search history.

(56) References Cited

U.S. PATENT DOCUMENTS

| | | | |
|---|---|---|---|
| 10,172,567 B2 | 1/2019 | Moxon et al. | |
| 2002/0103512 A1* | 8/2002 | Echauz ................ | A61B 5/076 607/9 |
| 2011/0082381 A1* | 4/2011 | Uthman ................. | A61B 5/726 600/544 |
| 2011/0257556 A1* | 10/2011 | Guo ...................... | A61B 5/4812 600/544 |
| 2019/0059769 A1 | 2/2019 | Nenadovic et al. | |

(Continued)

FOREIGN PATENT DOCUMENTS

| | | |
|---|---|---|
| CN | 104720796 | 10/2017 |
| CN | 107788967 | 3/2018 |
| CN | 108143409 | 6/2018 |

(Continued)

OTHER PUBLICATIONS

Varun Bajaj et al., "Classification of Seizure and Nonseizure EEG Signals Using Empirical Mode Decomposition", IEEE Transactions on Information Technology in Biomedicine, Nov. 2012, pp. 1135-1142.

(Continued)

*Primary Examiner* — Nicole F Lavert
(74) *Attorney, Agent, or Firm* — JCIP Global Inc.

(57) ABSTRACT

A method and a system for processing an electroencephalogram (EEG) signal are provided. The method for processing the EEG signal includes: performing a spike detection on the EEG signal to obtain a spike distribution waveform, performing an instantaneous frequency oscillation energy analysis on the EEG signal to obtain multiple energy distribution waveforms; performing a complexity analysis on the EEG signal to obtain a complexity change waveform, obtaining a determination result of a specified neural waveform based on the spike distribution waveform, the energy distribution waveforms, and the complexity change waveform, and outputting the determination result.

9 Claims, 7 Drawing Sheets

(56) References Cited

U.S. PATENT DOCUMENTS

2019/0143073 A1* 5/2019 Grossman ............ A61N 5/0622
600/28
2020/0107735 A1 4/2020 Osorio et al.

FOREIGN PATENT DOCUMENTS

| EP | 3656299 | 5/2020 |
| TW | I398238 | 6/2013 |
| TW | I538661 | 6/2016 |
| TW | 201633180 | 9/2016 |
| TW | I583356 | 5/2017 |
| TW | 201813583 | 4/2018 |
| TW | M567613 | 10/2018 |
| WO | 2015079264 | 6/2015 |

OTHER PUBLICATIONS

"Office Action of Taiwan Counterpart Application", dated Jan. 15, 2021, pp. 1-4.
"Search Report of Europe Counterpart Application", dated Jan. 19, 2021, p. 1-p. 8.

\* cited by examiner

METHOD AND SYSTEM FOR PROCESSING ELECTROENCEPHALOGRAM SIGNAL

BACKGROUND

Technical Field

The disclosure relates to a method for processing a signal, and in particular to a method for processing an electroencephalography (EEG) signal.

Description of Related Art

Current and commonly used methods for measuring brain activity are: electrocorticography (ECoG) and electroencephalography (EEG). The signals of ECoG and EEG are commonly known as brainwave signals, and the two principles for generating the signals are almost the same. The difference between an ECoG signal and an EEG signal is that the measurement of the ECoG signal uses a semi-invasive method in which the skull of a patient is opened and electrodes are laid flat on the cerebral cortex and under the subdural, and the measurement of the EEG signal uses a non-invasive method in which the brainwave is measured on the scalp.

The brainwave signals are most commonly used to diagnose epilepsy. During epilepsy onset, according to the features of epilepsy pathophysiology and the characteristics of the brainwave signals, epilepsy may be roughly divided into the following stages: inter-ictal, pre-ictal, irregular phase, and bursting phase. The stage between two seizures is referred to as "inter-ictal", and "pre-ictal", "irregular phase", and "bursting phase" belong to ictal phase of epilepsy onset. The irregular phase is of great significance for diagnosis and evaluation of epilepsy, but conventional algorithms are less able to effectively detect such characteristics. The reason is that the neurophysiological performance and the complex interaction between excitatory cells and suppressor cells enable the brainwave signals to exhibit non-stationary characteristics, such that the brainwave signals exhibit irregular frequency and irregular amplitude changes, which are difficult for conventional algorithm determination models to accurately interpret.

SUMMARY

The disclosure provides a method and a system for processing an electroencephalography (EEG) signal, which can accurately find a specified neural waveform in the EEG signal.

The method for processing the EEG signal of the disclosure performs the following steps through a processor. The EEG signal is obtained. A spike detection is performed on the EEG signal to obtain a spike distribution waveform. An instantaneous frequency oscillation energy analysis is performed on the EEG signal to obtain multiple energy distribution waveforms. A complexity analysis is performed on the EEG signal to obtain a complexity change waveform. A determination result of a specified neural waveform is obtained based on the spike distribution waveform, the energy distribution waveforms, and the complexity change waveform, wherein the determination result includes a time interval. A waveform in the time interval of the spike distribution waveform conforms to a spike distribution rule of the specified neural waveform. A waveform in the time interval of each energy distribution waveform conforms to an energy change rule of the specified neural waveform. A waveform in the time interval of the complexity change waveform conforms to a complexity change rule of the specified neural waveform.

In an embodiment of the disclosure, the step of performing the spike detection on the EEG signal to obtain the spike distribution waveform includes the following steps. The EEG signal is divided into multiple sampling intervals using a window width. A spike number included in each sampling interval is detected. In a spike distribution waveform diagram, the spike number included in each sampling interval is recorded following a time series, thereby obtaining the spike distribution waveform.

In an embodiment of the disclosure, after the spike distribution waveform is obtained, the method further includes the following steps. Whether spike numbers in multiple unit intervals of the spike distribution waveform conform to the spike distribution rule is determined. In two adjacent unit intervals in a time series, if a spike number in a later unit interval decreases compared with a spike number in an earlier unit interval, the later unit interval is determined as conforming to the spike distribution rule.

In an embodiment of the disclosure, the step of performing the instantaneous frequency oscillation energy analysis on the EEG signal to obtain the energy distribution waveforms includes the following steps. An empirical mode decomposition (EMD) is performed on the EEG signal to obtain multiple intrinsic mode signals. An instantaneous frequency of each intrinsic mode signal in each of multiple sampling intervals is calculated to record the instantaneous frequency corresponding to each sampling interval following a time series in an instantaneous frequency distribution diagram corresponding to each intrinsic mode signal, thereby obtaining multiple instantaneous frequency distribution waveforms respectively corresponding to the multiple intrinsic mode signals. An energy calculation is respectively performed on the multiple instantaneous frequency signals to obtain the multiple energy distribution waveforms.

In an embodiment of the disclosure, after the energy distribution waveform is obtained, the method further includes the following steps. Whether an energy density of each energy distribution waveform in multiple unit intervals conforms to the energy change rule is determined. In two adjacent unit intervals in a time series of each of the energy distribution waveforms at the same time, if an energy density in a later unit interval decreases compared with an energy density in an earlier unit interval, the later unit interval is determined as conforming to the energy change rule.

In an embodiment of the disclosure, the step of performing the complexity analysis on the EEG signal to obtain the complexity change waveform includes the following steps. The EEG signal is divided into multiple sampling intervals using a window width. A complexity of each sampling interval is calculated. In a complexity waveform diagram, the complexity corresponding to each sampling interval is recorded following a time series, thereby obtaining a complexity waveform. The complexity waveform is divided into multiple calculation intervals using another window width. A spike number included in each calculation interval is detected. In a complexity spike distribution diagram, the spike number included in each calculation interval is recorded following a time series, thereby obtaining the complexity change waveform.

In an embodiment of the disclosure, after the complexity change waveform is obtained, the method further includes the following step. Whether spike numbers in multiple unit intervals of the complexity change waveform conforms to the complexity change rule is determined. A unit interval in which the spike number is greater than a preset value is determined as conforming to the complexity change rule.

In an embodiment of the disclosure, the specified neural waveform is an irregular phase waveform for determining epilepsy onset.

The system for processing an EEG signal of the disclosure includes: an output device, a storage device, and a processor. The storage device includes multiple code fragments. The processor is coupled to the output device and the storage device. The processor performs the code fragments to: obtain the EEG signal; perform a spike detection on the EEG signal to obtain a spike distribution waveform; perform an instantaneous frequency oscillation energy analysis on the EEG signal to obtain multiple energy distribution waveforms; perform a complexity analysis on the EEG signal to obtain a complexity change waveform; and obtain a determination result of a specified neural waveform based on the spike distribution waveform, the energy distribution waveforms, and the complexity change waveform, wherein the determination result includes a time interval. A waveform in the time interval of the spike distribution waveform conforms to a spike distribution rule of the specified neural waveform. A waveform in the time interval of each energy distribution waveform conforms to an energy change rule of the specified neural waveform. A waveform in the time interval of the complexity change waveform conforms to a complexity change rule of the specified neural waveform.

Based on the above, the disclosure can accurately detect the irregular phase in the EEG signal by combining the spike detection, the instantaneous frequency oscillation energy analysis, and the complexity analysis.

To make the aforementioned and other features of the disclosure more comprehensible, several embodiments accompanied with drawings are described in detail as follows.

DETAILED DESCRIPTION OF DISCLOSED EMBODIMENTS

Figure 1:
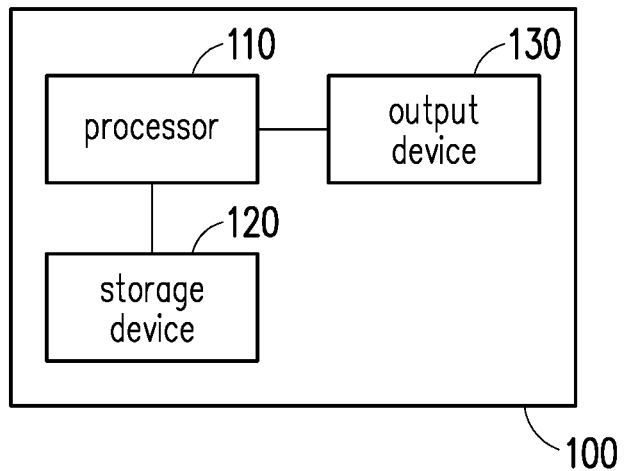
FIG. 1 is a block diagram of a system for processing an electroencephalogram (EEG) signal according to an embodiment of the disclosure.

FIG. 1 is a block diagram of a system for processing an electroencephalogram (EEG) signal according to an embodiment of the disclosure. In FIG. 1, a system for processing an EEG signal 100 is a device for analyzing an EEG signal. The system for processing an EEG signal 100 may be a computing device such as a desktop computer, a notebook computer, a smart phone, etc. The system for processing an EEG signal 100 includes a processor 110, a storage device 120, and an output device 130.

The processor 110 is, for example, a central processing unit (CPU), a physics processing unit (PPU), a programmable microprocessor, an embedded control chip, a digital signal processor (DSP), an application specific integrated circuits (ASIC), or other similar devices.

The storage device 120 is, for example, any type of fixed or removable random-access memory (RAM), read-only memory (ROM), flash memory, hard disk, other similar devices, or a combination of the aforementioned devices. Multiple code fragments are stored in the storage device 120. The code fragments are performed by the processor 110 after being installed to implement the method for processing the EEG signal described later.

The output device 130 is, for example, a display. When the processor 110 obtains a final determination result, the determination result may be transmitted to the output device 130. In addition, the processor 110 may also store the determination result in the storage device 120 or transmit the determination result to a server of a medical center through a communication device (not shown) via network.

Figure 2:
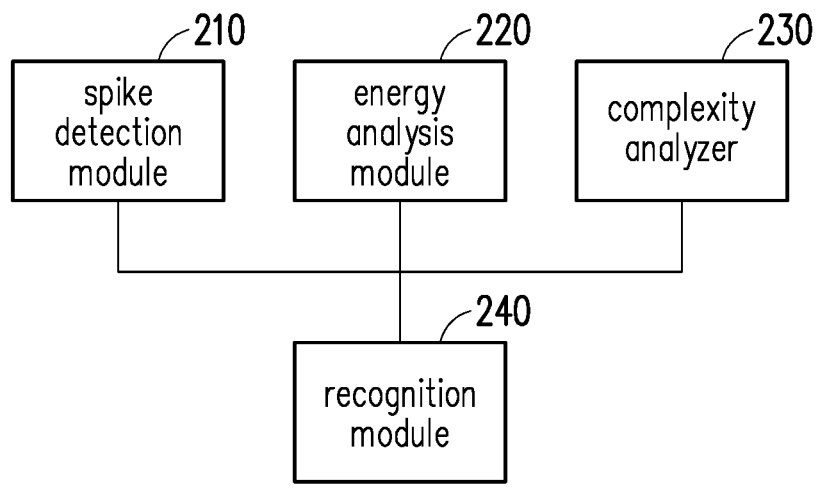
FIG. 2 is a block diagram of an EEG signal processing module according to an embodiment of the disclosure.

FIG. 2 is a block diagram of an EEG signal processing module according to an embodiment of the disclosure. The EEG signal processing module shown in FIG. 2 is, for example, composed of multiple program code fragments stored in the storage device 120. The EEG signal processing module includes a spike detection module 210, an energy analysis module 220, a complexity analyzer 230, and a recognition module 240. The spike detection module 210 is configured to perform a spike detection on the EEG signal. The energy analysis module 220 is configured to perform an instantaneous frequency oscillation energy analysis on the EEG signal. The complexity analyzer 230 is configured to perform a complexity analysis on the EEG signal. The recognition module 240 is configured to obtain a time interval of a specified neural waveform based on a spike distribution waveform, energy distribution waveforms, and a complexity change waveform. The specified neural waveform is an irregular phase waveform for determining epilepsy onset.

Figure 3:
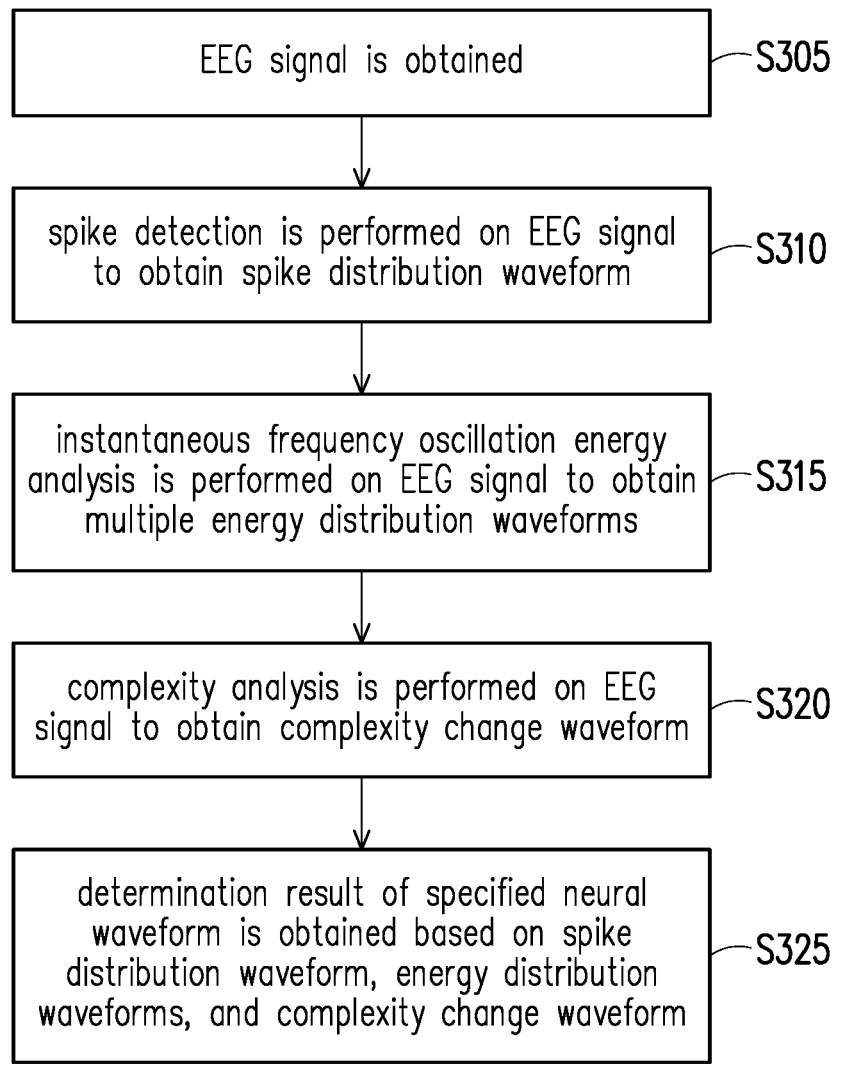
FIG. 3 is a flowchart of a method for processing an EEG signal according to an embodiment of the disclosure.
Figure 4:
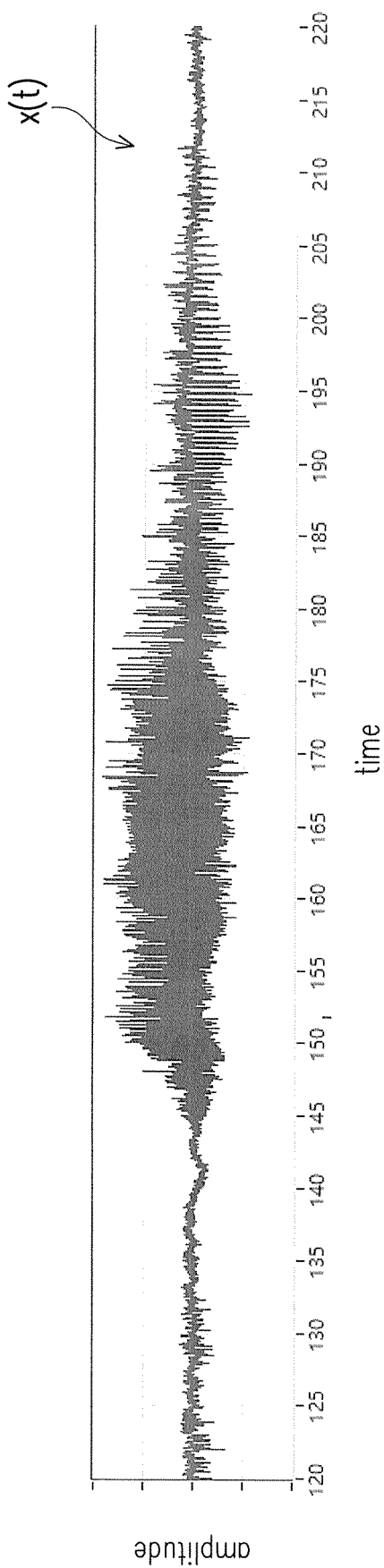
FIG. 4 is a waveform diagram of an EEG signal according to an embodiment of the disclosure.

FIG. 3 is a flowchart of a method for processing an EEG signal according to an embodiment of the disclosure. Please refer to FIG. 3, in Step S305, the EEG signal is obtained. For example, the EEG signal of a subject is extracted using an EEG measuring instrument, as shown in FIG. 4. FIG. 4 is a waveform diagram of an EEG signal according to an embodiment of the disclosure. An EEG signal x(t) obtained at this time is a time domain signal. Then, the system for processing an EEG signal 100 receives the EEG signal x(t) from the EEG measuring instrument, and the processor 110 analyzes the EEG signal x(t) through the EEG signal processing module (shown in FIG. 2).

Taking the time interval of the specified neural waveform as an irregular phase, the EEG signal processing module analyzes the pre-processed EEG signal x(t) via the spike detection module 210, the energy analysis module 220, and the complexity analyzer 230. Here, the pre-processing is, for example, band-pass filtering processing, noise filtering processing, re-sampling processing, time-series segmentation processing, etc.

The spike detection module 210, the energy analysis module 220, and the complexity analyzer 230 respectively calculate non-stationary waveform characteristics (characteristics of irregular phase) with a preset time-series window. After that, the spike detection module 210, the energy analysis module 220, and the complexity analyzer 230 transmit obtained results to the recognition module 240. The recognition module 240 interprets the specified neural waveform and finally outputs a result. The non-stationary waveform characteristics include: increased amplitude density (i.e., fewer oscillations, larger amplitude), frequency drift (wider frequency band, dominant frequency drift), larger waveform density spacing (relative to start of onset), and inconsistent spacings (disorder is too large).

The following Step S310, Step S315, and Step S320 are used to respectively illustrate the spike detection module 210, the energy analysis module 220, and the complexity analyzer 230. The steps may be performed simultaneously or separately, and the sequence of performing the steps is not limited herein.

Figure 5:
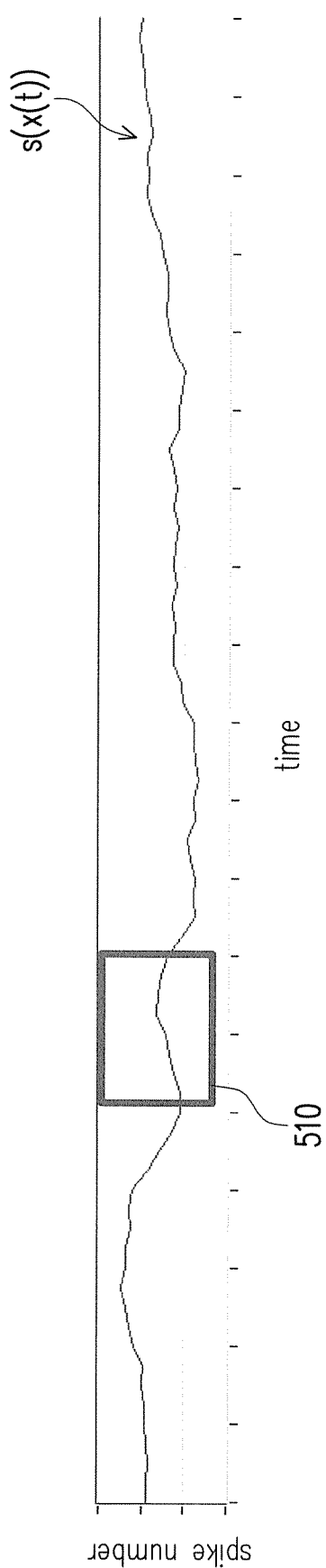
FIG. 5 is a spike distribution waveform diagram according to an embodiment of the disclosure.

In Step S310, the spike detection module 210 performs a spike detection on the EEG signal to obtain a spike distribution waveform. Here, the spike detection module 210 divides the EEG signal x(t) into multiple sampling intervals using a window width (first window width) to detect a spike number in each sampling interval. Next, the spike detection module 210 records the spike number included in each sampling interval following the time series in the spike distribution waveform diagram, thereby obtaining a spike distribution waveform s(x(t)), as shown in FIG. 5. FIG. 5 is a spike distribution waveform diagram according to an embodiment of the disclosure. For example, assuming that the window width is 5 seconds and taking a signal segment from 0 to 5 seconds in the EEG signal x(t), the number of spikes of the signal in 5 seconds is calculated. The spike number is projected to the $5^{th}$ second of the spike distribution waveform diagram shown in FIG. 5. By analogy, a spike number is recorded every 5 seconds. The time unit of the spike distribution waveform s(x(t)) is the window width (first window width).

Figure 6:
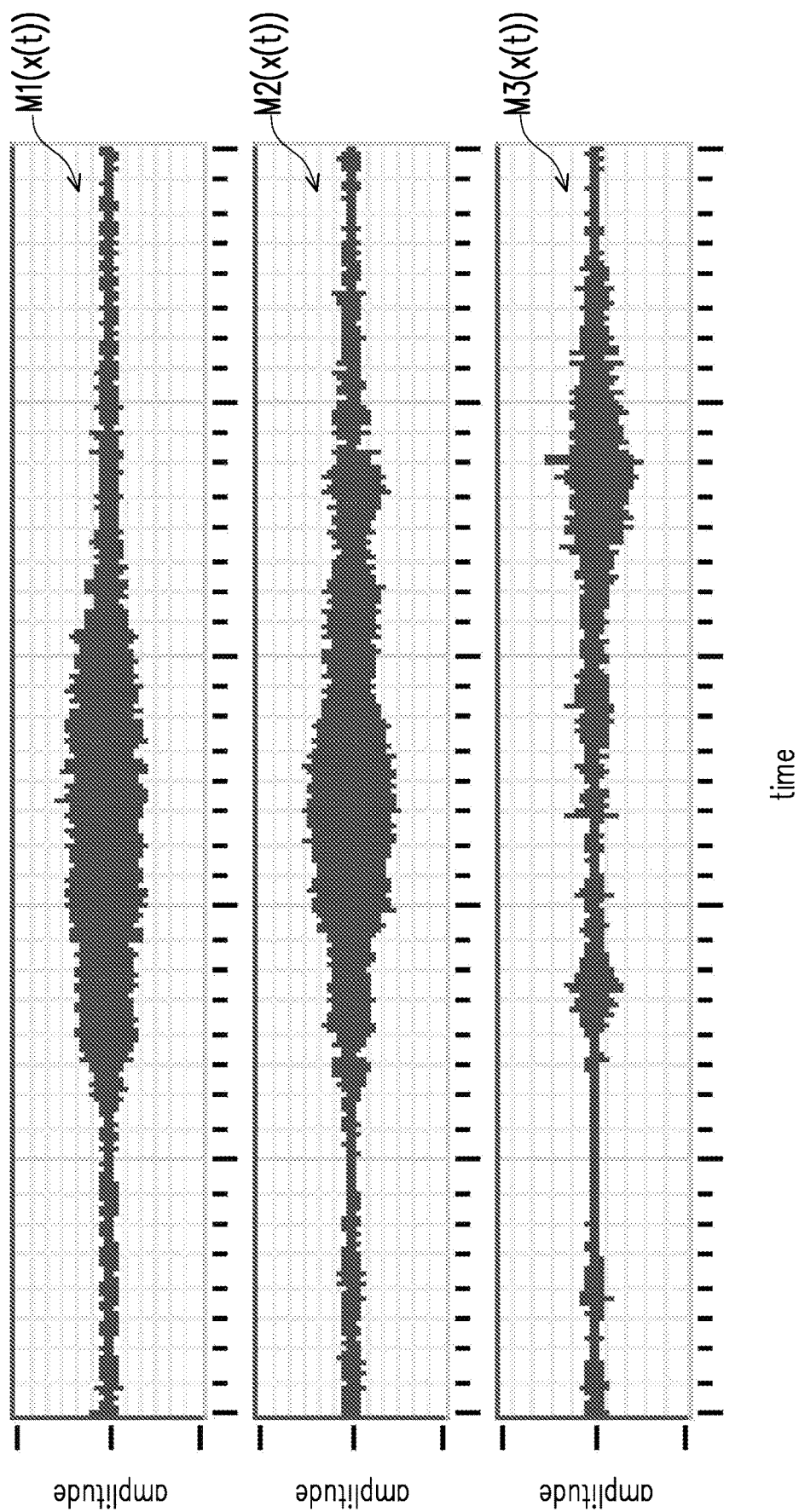
FIG. 6 is a waveform diagram of an intrinsic mode signal according to an embodiment of the disclosure.
Figure 7:
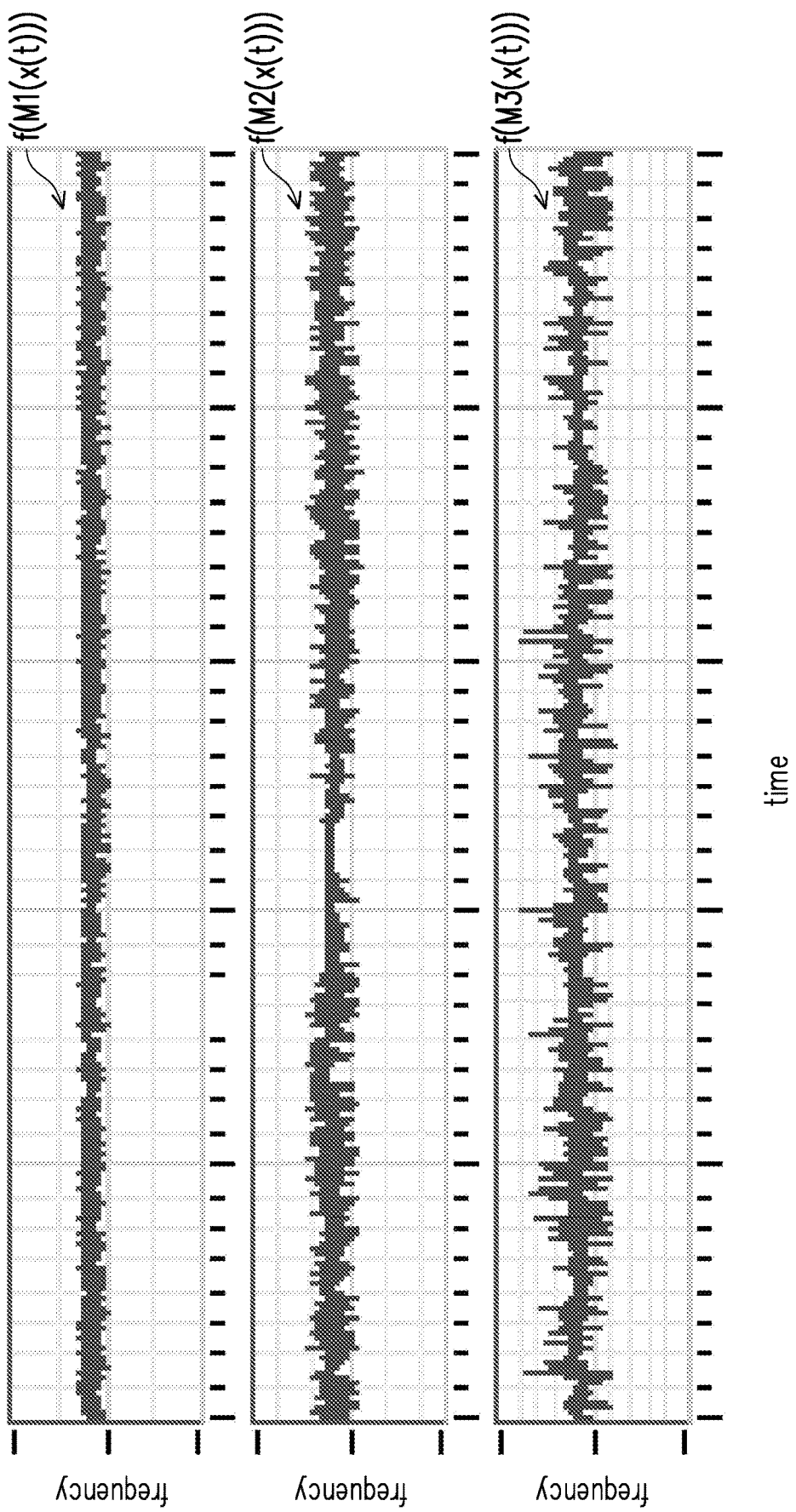
FIG. 7 is an instantaneous frequency distribution waveform diagram according to an embodiment of the disclosure.
Figure 8:
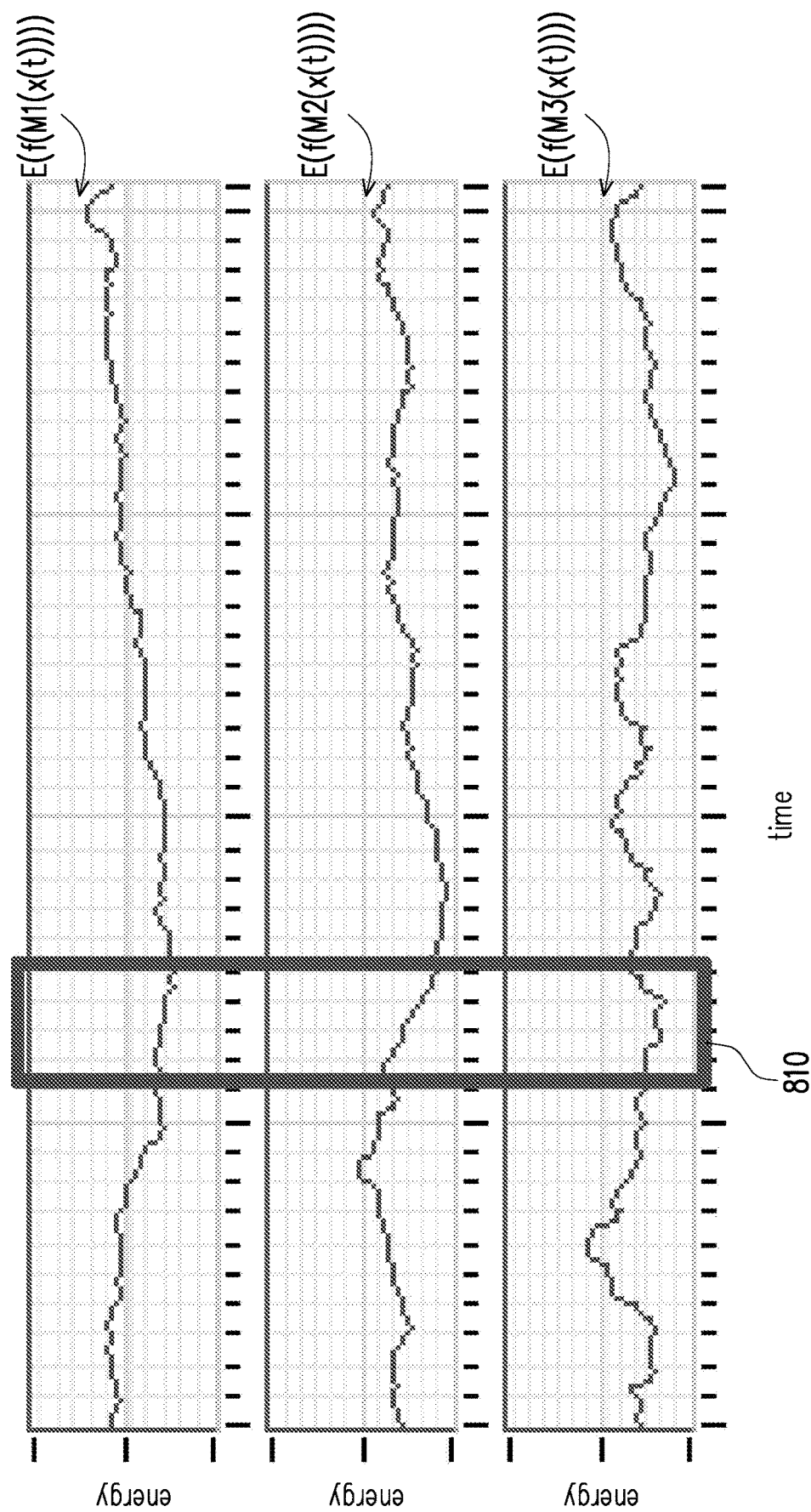
FIG. 8 is an energy distribution waveform diagram according to an embodiment of the disclosure.

In Step S315, the energy analysis module 220 performs an instantaneous frequency oscillation energy analysis on the EEG signal to obtain multiple energy distribution waveforms. The following is illustrated with FIG. 6, FIG. 7, and FIG. 8. FIG. 6 is a waveform diagram of an intrinsic mode signal according to an embodiment of the disclosure. FIG. 7 is an instantaneous frequency distribution waveform diagram according to an embodiment of the disclosure. FIG. 8 is an energy distribution waveform diagram according to an embodiment of the disclosure.

The energy analysis module 22 decomposes the EEG signal x(t) to be analyzed into multiple intrinsic mode signals (in the embodiment, three intrinsic modes signals M1(x(t)), M2(x(t)), and M3(x(t)) are exemplified for illustration) by performing an empirical mode decomposition (EMD) method.

Next, the energy analysis module 22 calculates an instantaneous frequency of each of the intrinsic mode signals M1(x(t)), M2(x(t)), and M3(x(t)) in each of multiple sampling intervals. Here, in terms of the intrinsic mode signal M1(x(t)), the intrinsic mode signal M1(x(t)) is divided into multiple sampling intervals using a window width (second window width). Then, the instantaneous frequency of the signal in each sampling interval is calculated, for example, using the Hilbert transform, thereby obtaining an instantaneous frequency distribution waveform f(M1(x(t))) shown in FIG. 7. By analogy, the intrinsic mode signal M2(x(t)) and the intrinsic mode signal M3(x(t)) are respectively converted into an instantaneous frequency distribution waveform f(M2(x(t))) and an instantaneous frequency distribution waveform f(M3(x(t))). That is, in an instantaneous frequency distribution diagram corresponding to each intrinsic mode signal, the instantaneous frequency corresponding to each sampling interval is recorded following the time series, thereby obtaining the instantaneous frequency distribution waveform corresponding to each intrinsic mode signal.

After that, the energy analysis module 22 respectively performs energy calculations on the multiple instantaneous frequency signals f(M1(x(t))), f(M2(x(t))), and f(M3(x(t))) to obtain multiple energy distribution waveforms E(f(M1(x(t)))), E(f(M2(x(t)))), and E(f(M3(x(t)))), as shown in FIG. 8. For example, the energy calculated by the energy analysis module 22 is spectral energy density or power spectral density.

Figure 9:
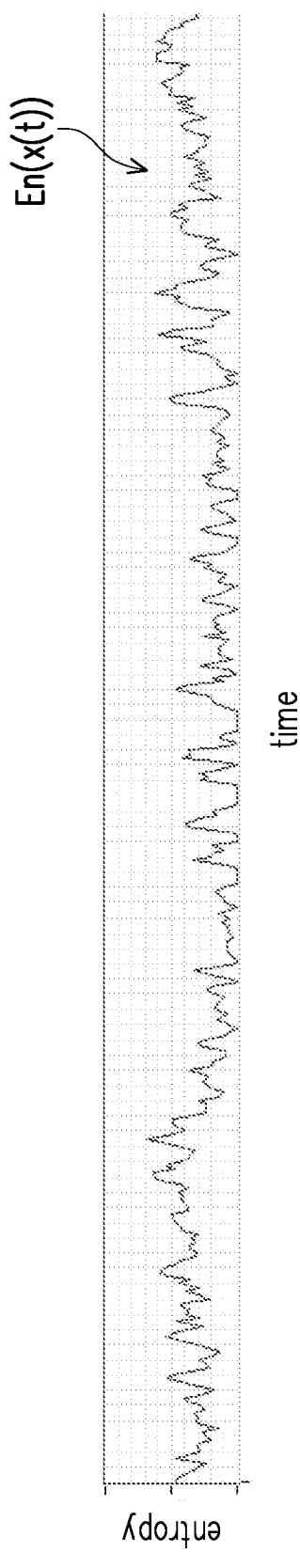
FIG. 9 is a complexity waveform diagram according to an embodiment of the disclosure.
Figure 10:
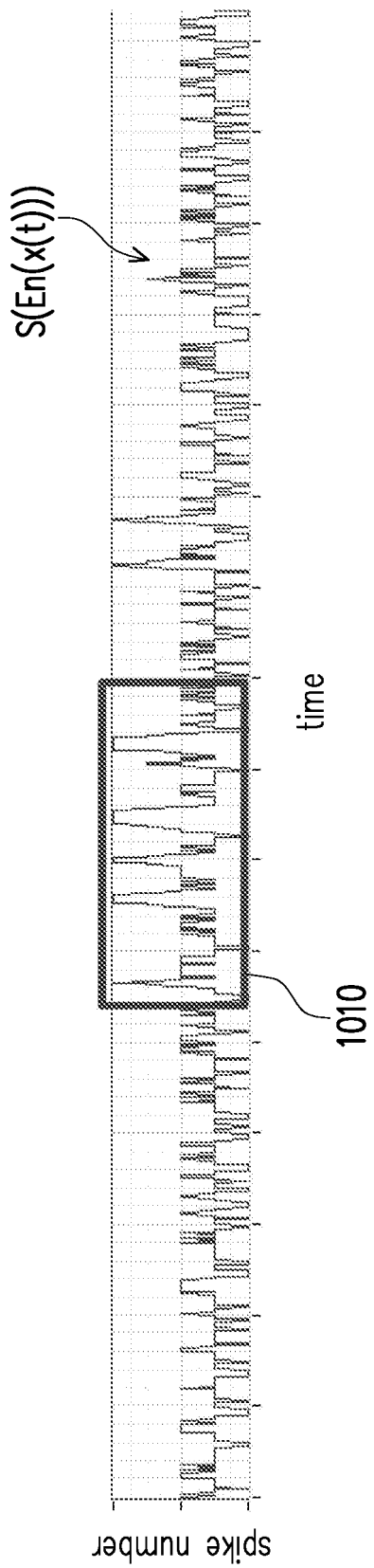
FIG. 10 is a complexity spike distribution diagram according to an embodiment of the disclosure.

In Step S320, the complexity analyzer 230 performs a complexity analysis on the EEG signal to obtain a complexity change waveform. The following is illustrated with FIG. 9 and FIG. 10. FIG. 9 is a complexity waveform diagram according to an embodiment of the disclosure. FIG. 10 is a complexity spike distribution diagram according to an embodiment of the disclosure.

The complexity analyzer 230 divides the EEG signal x(t) into multiple sampling intervals using a window width (third window width) to calculate a complexity of each sampling interval. The third window width is, for example, 1 second. Here, the complexity analyzer 230 calculates an entropy of each sampling interval. In a complexity waveform diagram, the complexity analyzer 230 records the complexity (entropy) corresponding to each sampling interval following the time series, thereby obtaining a complexity waveform En(x(t)).

The entropy is, for example, an approximate entropy (ApEn). The approximate entropy is a mathematical method for analyzing the complexity of time-series connotation information. By calculating an entropy value of a signal at different time-space scales, a quantified standard for testing the complexity of the signal is provided. The approximate entropy calculates self-similarity difference of two adjacent time scales in a sampling interval. The higher the complexity, the higher the self-similarity ratio at a difference of one scale.

Next, the complexity analyzer 230 divides the complexity waveform En(x(t)) into multiple calculation intervals using another window width (fourth window width). The complexity analyzer 230 detects the spike number included in each calculation interval, and records the spike number included in each calculation interval following the time series in the complexity spike distribution diagram shown in FIG. 10, thereby obtaining a complexity change waveform S(En(x(t))). The fourth window width is, for example, 7 seconds. The complexity analyzer 230 takes a signal segment from 0 to 7 seconds in a complexity waveform En(x(t)), calculates the number of spikes of the signal in 7 seconds, and projects the obtained spike number to the $7^{th}$ second of the complexity spike distribution diagram shown in FIG. 10. By analogy, a spike number is recorded every 7 seconds. The time unit of the complexity change waveform S(En(x(t))) is the fourth window width.

In Step S325, the recognition module 240 obtains a determination result of the specified neural waveform based on the spike distribution waveform s(x(t)), the energy distribution waveforms E(f(M1(x(t)))), E(f(M2(x(t)))), and E(f(M3(x(t)))), and the complexity change waveform S(En(x(t))). The determination result includes a time interval where the specified neural waveform is located in the EEG signal. A waveform in the time interval of the spike distribution waveform s(x(t)) conforms to the spike distribution rule of the specified neural waveform. Waveforms in the time intervals of all the energy distribution waveforms E(f(M1(x(t)))), E(f(M2(x(t)))), and E(f(M3(x(t)))) conform to the energy change rule of the specified neural waveform. A waveform in the time interval of the complexity change waveform S(En(x(t))) conforms to the complexity change rule of the specified neural waveform.

Specifically, after obtaining the spike distribution waveform s(x(t)), the energy distribution waveforms E(f(M1(x(t)))), E(f(M2(x(t)))), and E(f(M3(x(t)))), and the complexity change waveform S(En(x(t))), the recognition module 240 determines whether the waveforms conform to the corresponding rule one by one according to a preset unit interval.

The recognition module 240 determines whether the spike numbers in multiple unit intervals of the spike distribution waveform s(x(t)) conform to the spike distribution rule. In two adjacent unit intervals in the time series, if the spike number in a later unit interval decreases compared with the spike number in an earlier unit interval, the later unit interval is determined as conforming to the spike distribution rule. In this way, the spike detection module 210 determines whether the spike numbers decrease. For example, the waveform in an interval 510 shown in FIG. 5 is determined as conforming to the spike distribution rule.

For example, assuming that 10 seconds is used as the unit interval for determination, and the spike number (total number of spikes) included in a first unit interval of 0 to 10 seconds is 30 and the spike number (total number of spikes) included in a second unit interval of 10 to 20 seconds is 10, the second unit interval is determined as conforming to the spike distribution rule. By analogy, the recognition module 240 discriminates whether each unit interval of the spike distribution waveform s(x(t)) conforms to the spike distribution rule. Moreover, the recognition module 240 sets a boolean value corresponding to the unit interval conforming to the spike distribution rule as "true" and sets the boolean value corresponding to the unit interval not conforming to the spike distribution rule as "false".

Moreover, the recognition module 240 further determines whether energy densities in multiple unit intervals of the energy distribution waveforms E(f(M1(x(t)))), E(f(M2(x(t)))), and E(f(M3(x(t)))) conform to the energy change rule. In two adjacent unit intervals in the time series of each of the energy distribution waveforms at the same time, if the energy density in a later unit interval decreases compared with the energy density in an earlier unit interval, the later unit interval is determined as conforming to the energy change rule. In other words, only in the case where the energy densities in the same unit interval of all three of the energy distribution waveforms E(f(M1(x(t)))), E(f(M2(x(t)))), and E(f(M3(x(t)))) decrease, the unit interval is determined as conforming to the energy change rule. For example, the waveform in an interval 810 shown in FIG. 8 is determined as conforming to the energy change rule. Moreover, the recognition module 240 sets the boolean value corresponding to the unit interval conforming to the energy change rule as "true" and sets the boolean value corresponding to the unit interval not conforming to the energy change rule as "false".

In addition, the recognition module 240 further determines whether the spike numbers in multiple unit intervals of the complexity change waveform S(En(x(t))) conforms to the complexity change rule. The unit interval in which the spike number is greater than a preset value is determined as conforming to the complexity change rule. For example, the spike number of the waveform in an interval 1010 shown in FIG. 10 is greater than the preset value, so the interval 1010 is determined as conforming to the complexity change rule. Moreover, the recognition module 240 sets the boolean value corresponding to the unit interval conforming to the complexity change rule as "true" and sets the boolean value corresponding to the unit interval not conforming to the complexity change rule as "false".

Finally, the recognition module 240 finds the unit intervals corresponding to the boolean values that are all "true" in multiple unit intervals included in each of the spike distribution waveform s(x(t)), the energy distribution waveforms E(f(M1(x(t)))), E(f(M2(x(t)))), and (f(M3(x(t)))), and the complexity change waveform S(En(x(t))), which represents the time interval where the specified neural waveform is located. For example, assuming that the boolean value corresponding to the unit interval from 100 to 110 seconds of the spike value distribution waveform s(x(t)) is "true", the boolean values corresponding to the unit interval from 100 to 110 seconds of all three of the energy distribution waveforms E(f (M1(x(t)))), E(f(M2(x(t)))), and E(f(M3(x(t)))) are "true", and the boolean value corresponding to the unit interval from 100 to 110 seconds of the complexity change waveform S(En(x(t))) is "true", the unit interval from 100 to 110 seconds is determined as the time interval where the specified neural waveform is located, that is, the irregular phase.

In summary, the disclosure combines the spike detection, the instantaneous frequency oscillation energy analysis, and the complexity analysis, and uses the discrimination of the spike distribution waveform to find pre-ictal and post-ictal characteristic identification. Also, in terms of the discrimination of the energy distribution waveforms, characteristic identification between the irregular phase and the onset can be distinguished. In addition, in terms of the discrimination of the complexity change waveform, characteristic identification of the irregular phase and the bursting phase can be distinguished. As such, the irregular phase in the EEG signal can be accurately found.

Although the disclosure has been disclosed in the above embodiments, the embodiments are not intended to limit the disclosure. It will be apparent to persons skilled in the art that various modifications and variations can be made to the disclosed embodiments without departing from the scope or spirit of the disclosure. In view of the foregoing, it is intended that the disclosure covers modifications and variations provided that they fall within the scope of the following claims and their equivalents.

What is claimed is:
1. A method for processing an electroencephalography (EEG) signal, through a processor, comprising:
    obtaining the EEG signal;
    dividing the EEG signal into a plurality of first sampling intervals, and detecting a spike number comprised in each of a plurality of first sampling intervals to obtain a spike distribution waveform;
    decomposing the EEG signal into a plurality of intrinsic modes signals, dividing each of the intrinsic modes signals into a plurality of second sampling intervals, calculating an instantaneous frequency in each of the second sampling intervals to obtain a plurality of instantaneous frequency distribution waveforms respectively corresponding to the plurality of intrinsic mode signals, and respectively performing an energy calculation on the instantaneous frequency distribution waveforms to obtain a plurality of energy distribution waveforms;

dividing the EEG signal into a plurality of third sampling intervals, calculating an entropy of each of the third sampling intervals to obtain a complexity waveform, dividing the complexity waveform into a plurality of calculation intervals, and detecting a spike number comprised in each of the calculation intervals to obtain a complexity change waveform; and obtaining a determination result of a specified neural waveform based on the spike distribution waveform, the plurality of energy distribution waveforms, and the complexity change waveform, wherein the determination result comprises a time interval, wherein obtaining the determination result of the specified neural waveform based on the spike distribution waveform, the plurality of energy distribution waveforms, and the complexity change waveform comprises:

dividing each of the spike distribution waveform, the plurality of energy distribution waveforms, and the complexity change waveform into a plurality of unit intervals in a time series;

determining whether a first total number of spikes in each of the unit intervals in the spike distribution waveform conforms to a spike distribution rule;

determining whether an energy density in each of the unit intervals in each of the energy distribution waveforms conforms to an energy change rule;

determining whether a second total number of spikes in each of the unit intervals in the complexity change waveform conforms to a complexity change rule; and finding a plurality of continuous unit intervals, conforming to the spike distribution rule, the energy change rule and the complexity change rule, in the respective plurality of unit intervals included in the spike wave distribution waveform, the energy distribution waveforms, and the complexity change waveform, and using the plurality of continuous unit intervals as the time interval where the specified neural waveform is located.

2. The method for processing an EEG signal according to claim 1, wherein obtaining the spike distribution waveform comprises:

recording the spike number comprised in each of the first sampling intervals following the time series in a spike distribution waveform diagram, thereby obtaining the spike distribution waveform.

3. The method for processing an EEG signal according to claim 1, wherein determining whether the first total number of spikes in each of the unit intervals in the spike distribution waveform conforms to the spike distribution rule comprises:

in two adjacent unit intervals in the spike distribution waveform, if a first total number of spikes in a later unit interval decreases compared with a first total number of spikes in an earlier unit interval, determining the later unit interval as conforming to the spike distribution rule.

4. The method for processing an EEG signal according to claim 1, wherein the step of decomposing the EEG signal into the plurality of intrinsic modes signals comprises:

performing an empirical mode decomposition on the EEG signal to obtain the intrinsic mode signals;

wherein obtaining the plurality of energy distribution waveforms comprises:

recording the instantaneous frequency corresponding to each of the second sampling intervals following the time series in an instantaneous frequency distribution diagram corresponding to each of the intrinsic mode signals, thereby obtaining the instantaneous frequency distribution waveforms respectively corresponding to the plurality of intrinsic mode signals.

5. The method for processing an EEG signal according to claim 1, wherein determining whether the energy density in each of the unit intervals in each of the energy distribution waveforms conforms to the energy change rule comprises:

in two adjacent unit intervals in each of the energy distribution waveforms at a same time, if an energy density in a later unit interval decreases compared with an energy density in an earlier unit interval, determining the later unit interval as conforming to the energy change rule.

6. The method for processing an EEG signal according to claim 1, wherein obtaining the complexity waveform comprises:

recording the entropy corresponding to each of the third sampling intervals following a time series in a complexity waveform diagram, thereby obtaining a complexity waveform;

wherein obtaining the complexity change waveform comprises:

recording the spike number comprised in each of the calculation intervals following a time series in a complexity spike distribution diagram, thereby obtaining the complexity change waveform.

7. The method for processing an EEG signal according to claim 1, wherein determining whether the second total number of spikes in each of the unit intervals in the complexity change waveform conforms to the complexity change rule comprises:

determining a unit interval in which the second total number of spikes is greater than a preset value as conforming to the complexity change rule.

8. The method for processing an EEG signal according to claim 1, wherein the specified neural waveform is an irregular phase waveform for determining epilepsy onset.

9. A system for processing an EEG signal, comprising:
an output device;
a storage device, comprising a plurality of code fragments; and
a processor, coupled to the output device and the storage device, the processor performing the plurality of code fragments to:
obtain the EEG signal;
dividing the EEG signal into a plurality of first sampling intervals, and detecting a spike number comprised in each of a plurality of first sampling intervals to obtain a spike distribution waveform;
decomposing the EEG signal into a plurality of intrinsic modes signals, dividing each of the intrinsic modes signals into a plurality of second sampling intervals, calculating an instantaneous frequency in each of the second sampling intervals to obtain a plurality of instantaneous frequency distribution waveforms respectively corresponding to the plurality of intrinsic mode signals, and respectively performing an energy calculation on the instantaneous frequency distribution waveforms to obtain a plurality of energy distribution waveforms;
dividing the EEG signal into a plurality of third sampling intervals, calculating an entropy of each of the third sampling intervals to obtain a complexity waveform, dividing the complexity waveform into a plurality of calculation intervals, and detecting a spike number comprised in each of the calculation intervals to obtain a complexity change waveform; and obtain a determination result of a specified neural waveform based on the spike distribution waveform, the plurality of energy distribution waveforms, and the complexity change waveform, wherein the determination result comprises a time interval, wherein the processor is configured to:

divide each of the spike distribution waveform, the plurality of energy distribution waveforms, and the complexity change waveform into a plurality of unit intervals in a time series;

determine whether a first total number of spikes in each of the unit intervals in the spike distribution waveform conforms to a spike distribution rule;

determine whether an energy density in each of the unit intervals in each of the energy distribution waveforms conforms to an energy change rule;

determine whether a second total number of spikes in each of the unit intervals in the complexity change waveform conforms to a complexity change rule; and find a plurality of continuous unit intervals, conforming to the spike distribution rule, the energy change rule and the complexity change rule, in the respective plurality of unit intervals included in the spike wave distribution waveform, the energy distribution waveforms, and the complexity change waveform, and using the plurality of continuous unit intervals as the time interval where the specified neural waveform is located.

* * * * *